United States Patent [19]

Carr

[11] 4,103,021
[45] Jul. 25, 1978

[54] METHOD OF LOWERING BLOOD LIPID LEVELS IN MAMMALS

[75] Inventor: John B. Carr, Modesto, Calif.

[73] Assignee: Shell Oil Company, Houston, Tex.

[21] Appl. No.: 779,648

[22] Filed: Mar. 21, 1977

[51] Int. Cl.$^2$ .................. A61K 31/335; A61K 31/35
[52] U.S. Cl. .................................... 424/278; 424/283
[58] Field of Search ............................... 424/278, 283

[56] References Cited

PUBLICATIONS

Koo et al., J. Am. Chem. Soc. 77, 5373 (1955).

*Primary Examiner*—Leonard Schenkman

[57] ABSTRACT

Levels of lipids in the blood of mammals are lowered by certain benzodioxin and benzopyran carboxamides.

1 Claim, No Drawings

METHOD OF LOWERING BLOOD LIPID LEVELS IN MAMMALS

Description of the Invention

It has been found that the levels of lipids in the blood of a mammal are lowered by administering to the mammal an effective amount of a compound of the formula:

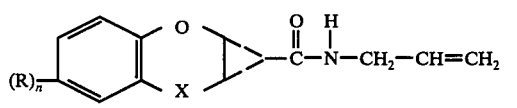

wherein n is zero or one, R is lower halogen, and X is —O— or —CH$_2$—.

By lower halogen is meant chlorine, fluorine and bromine; chlorine is preferred.

In formula I, the dotted lines from the free bond of the aminocarbonyl moiety to the carbon atoms in the 2-and 3-positions of the ring structure indicate that the contemplated compounds include those wherein the aminocarbonyl moiety is bonded to the ring at the 2-position, as well as those wherein it is bonded to the ring at the 3-position.

Chirality exists in the compounds of Formula I due to the asymmetric structural configuration at the carbon atom to which the aminocarbonyl moiety is bonded. As a result, two optical isomers of the compounds of Formula I exist. At the time this application is filed, no attempt has been made to separate and determine the lipogenesis inhibition activity of the individual optical isomers. Under the circumstances, the invention contemplates the individual optical isomers, as well as mixtures thereof.

The compound of Formula I wherein n is zero and X is —O— is known: J. Koo et al., J. Am. Chem. Soc., 77, 5373 (1955). The compounds of Formula I wherein n is one, X is —O—, and the aminocarbonyl moiety is bonded to the ring at the 2-position can be prepared by condensing a 4-halocatechol with ethyl 2,3-dibromopropionate by the method described in DeMarchi et al., Gazz. Chim. Ital., 95, 1447–54 (1965), to form the ethyl ester of 2,3-dihydro-6-halo-1,4-benzodioxin-2-carboxylic acid, then treating that ester with 2-propenamine by the method described in Koo et al., supra. A mixture of the 6- and 7-chloro esters can be formed. Treatment of the mixture with the amine forms a mixture of the 6- and 7-chloro carboxamides, which can be separated.

Thus, such compounds of Formula I can be prepared by heating an alkyl, suitably methyl or ethyl, ester of the corresponding carboxylic acid, in solution in a suitable solvent such as ethanol, with 2-propenamine. The reaction will go forward at room temperature, however, higher temperatures — for example, the mixtures can be refluxed — may be employed to reduce the reaction time. This procedure is described in the article by Koo, et al. Preferably, about a four-to-six-fold excess of the amine is used. The desired product can be recovered by evaporating the solvent and excess amine, then employing conventional techniques, such as selective extraction, recrystallization and/or dry-column chromatography, to isolate the desired product. Use of these procedures and techniques in particular instances is illustrated in the working examples included hereinafter.

Alternatively, the amides can be prepared by treating the corresponding carboxylic acid with thionyl chloride, to form the corresponding acid chloride, then treating the acid chloride with the amine. This procedure also is described in the article by Koo, et al. An excess of the thionyl chloride is used, in part acting as solvent. Conveniently, the treatment is conducted by refluxing the mixture. The excess thionyl chloride then is evaporated and the acid chloride can be isolated. Alternatively, the crude product can be treated with an excess of the amine, a solvent such as methylene chloride being added if needed to moderate the reaction and/or to ensure a liquid reaction mixture. The amide product can be recovered from the reaction mixture as indicated above.

The precursor catechols (R = H, 4-chlorine) are known compounds; others can be prepared as follows, referring to the substituent, R, n being one, and the position on the catechol ring:

R = 4—Br. Bromination of catechol, with dioxane dibromide, using the procedure of Yanovskaya et al., Zhur. Ohschei, Khim. (J. Gen. Chem.) 22, 1594 (1952) (Chemical Abstracts, 47, 8033b).

R —4—F. The method of Corse et al., J. Org. Chem., 16, 1345 (1951) (Chem. Abst., 46, 6095b).

Compounds of Formula I wherein X is —CH$_2$—can be prepared in a similar manner from precursor acid esters or chlorides and 2-propenamine.

Precursor acids and esters for preparing compounds of Formula I wherein the aminocarbonyl moiety is bonded at the 2-position of the ring structure are disclosed in Witiak et al., J. Med. Chem., 14, 758—66 (1971); and Witiak et al., Jr. Med. Chem., 18, 934–42 (1975). Taylor et al., J. Chem. Soc. London, discloses 2H-1-benzopyran-3-carboxylic acid which can be hydrogenated to form the precursor acid wherein the aminocarbonyl moiety is bonded at the 3-position of the ring, and n = 0.

Other precursor carboxylic acids and esters can be prepared by analogous methods:

(a) those acids wherein the carboxy moiety is bonded at the 2-position of the ring can be prepared by treating the appropriate 4-R-phenol with alpha-bromo-gramma-butyrolactone to form the 3-(4-R-phenoxy)dihydro-2(3H)-furanone; treating that furanone with Jones reagent to form the 2-(4-R-phenoxy)butanedioic acid; cyclizing that acid with sulfuric acid to form the 6-R-3,4-dihydro-4-oxo-2H-1-benzopyran-2-carboxylic acid; and hydrogenating (zinc-mercury amalgam, hydrochloric acid) to the desired carboxylic acid precursor.

(b) those esters wherein the alkoxycarbonyl moiety is bonded at the 3-position of the ring structure can be prepared by treating the appropriate halosalicylaldehyde with acrylonitrile (aqueous sodium hydroxide) to form the 6-halo-3,4-dihydro-4-hydroxy-2H-1-benzopyran-3-carbonitrile; heating with methanol and hydrochloric acid to form the methyl ester of the 6-halo-2-H-1-benzopyran-3-carboxylic acid; and hydrogenating (hydrogen, methanol, 10% palladium/carbon catalyst) to form the needed ester precursor.

The procedures for preparing compounds of Formula I are illustrated in Examples 1-4, following. In each case, the identities of the product and of the precursor(s) involved were confirmed by appropriate chemical and spectral analyses.

EXAMPLE 1 —
2,3-dihydro-N-(2-propenyl)-1,4-benzodioxin-2-carboxamide (1)

A solution of 5.2 g of the ethyl ester of 1,4-benzodioxan-2-carboxylic acid (Koo et al., supra) and 5.7 g of 2-propenamine in 50 ml of ethanol was refluxed for 20 hours. The solvent then was stripped off, and the residue was treated with charcoal and crystallized from ether-hexane to give 1, as white needles, m.p.: 55.5°–57° (Koo et al.: 59-61°).

EXAMPLE 2 -
6-chloro-2,3-dihydro-N-(2-propenyl)-1,4-benzodioxin-2-carboxamide (2)

4-chlorocatechol was condensed with ethyl 2,3-dibromopropionate by the method shown in F. DeMarchi, et al., supra. The product was a mixture of isomers: approximately 70% of the 7-chloro-isomer and 30% of the 6-chloro-isomer of the ethyl ester of 2,3-dihydro-1,4-benzodioxin-2-carboxylic acid. A solution of 10 g of this product and 9.1 g of 2-propenamine in 50 ml of ethanol was refluxed for 20 hours. The solvent then was stripped and the resulting gum was dry column chromatographed through silica gel using Solvent No. 3 (a 4:30:66 by volume mixture of tetrahydrofuran, ethyl acetate and hexane) as eluent. Workup, followed by repeated recrystallizations from ether-hexane, gave 2, as a white crystalline solid, m.p.: 72°–73°.

EXAMPLE 3 —
6-chloro-3,4-dihydro-N-(2-propenyl)-2H-1-benzopyran-2-carboxamide (3)

A solution of 3.1 g of 6-chloro-3,4-dihydro-2H-1-benzopyran-2-carboxylic acid (1A) Witiak et al., (1971), supra) in 15 ml of thionyl chloride was refluxed for 45 minutes. The excess thionyl chloride then was stripped off and the residual liquid was taken up in 50 ml of methylene chloride. To this stirred solution was added dropwise a solution of 2.5 g of 2-propenamine in 10 ml of methylene chloride. The resulting mixture was stirred at room temperature overnight, then washed with water, dried ($MgSO_4$) and stripped of solvent. Dry column chromatography of the solid product through silica gel, using Solvent No. 3 as eluent, followed by recrystallization of the product from methylene chloride and hexane gave 3, as a pale yellow solid, m.p.: 112.5°–114°.

EXAMPLE 4 —
3,4-dihydro-N-(2-propenyl)-2H-1-benzopyran-3-carboxamide (4)

A solution of 10.4 g of the methyl ester of 2H-1-benzopyran-3-carboxylic acid (Taylor et al., supra) in 50 ml of methanol containing 300 mg of 10% palladium on carbon catalyst, was hydrogenated in a Parr apparatus for 1.5 hours, at an initial pressure of 44 psig. The mixture then was filtered through a Celite pad to remove the catalyst, the filtrate was stripped of solvent and the product was vacuum distilled to give the methyl ester of 3,4-dihydro-2H-1-benzopyrancarboxylic acid (4A), as a colorless liquid, b.p.: 86°–88° (0.01 Torr.).

A solution of 5 g of 4A and 5.7 g of 2-propenamine in 50 ml of ethanol was refluxed for 6 days. Stripping of the solvent, followed by charcoal treatment of the product and recrystallization of the treated product from ether-hexane, gave 2, as white crystals, m.p.: 114.5°–115.5°.

EXAMPLE 5 —
6-chloro-3,4-dihydro-N-(2-propenyl)-2H-1-benzopyran-3-carboxamide (5)

To a stirred, refluxing mixture of 50 g of 3-chloro-6-hydroxybenzaldehyde and 62 ml of acrylonitrile in 50 ml of water was added dropwise over a three-hour period a solution of 12.8 g of sodium hydroxide in 120 ml of water. Then an additional 62 ml of acrylonitrile was added and the stirred mixture was refluxed for 2 hours, then allowed to stand at room temperature overnight. The crystals which formed were filtered off, washed with water and dried to give a solid, which was dissolved in ethanol. The solution was cooled and filtered to give 6-chloro-3,4-dihydro-4-hydroxy-(2H)-1-benzopyran-3-carbonitrile (5A), a solid. A mixture of 5A with 250 ml of methanol containing 2 ml of sulfuric acid, was refluxed for 4 days and stripped of solvent. The resulting residue was dry column chromatographed over silica gel, using Solvent No. 3 as eluent. The product obtained on workup was recrystallized from ether to give methyl 6-chloro-2H-1-benzopyran-3-carboxylate (5B), as light yellow needles, m.p.: 106°–109°.

700 mg of 5B was dissolved in 75 ml of ethyl acetate and the solution was treated with hydrogen (initial pressure of 30 psig), in the presence of a 10% palladium-on-carbon catalyst, for 8 hours. The reaction mixture then was filtered and stripped of solvent to give methyl 6-chloro-3,4-dihydro-2H-1-benzopyran-3-carboxylate (5C), as a yellow liquid, boiling point not determined.

A mixture of 500 mg of 5C, 5 ml of 2-propenamine and 25 ml of ethanol was refluxed for 18 hours. The solvent was then stripped off and the residue was taken up in methylene chloride, treated with hexane and cooled to give a solid. The solid was redissolved in ethanol, the solution was passed through a short silica gel column and the eluent was stripped of solvent. The residue was recrystallized from methylene chloride/hexane to give 5, as white needles, m.p.: 171°–171.5°.

Carboxamides of Formula I are of interest for reducing, and can be used to reduce, the amounts of lipids, particularly cholesterol and triglycerides, in the blood stream of mammals, such as, for example, pets, animals in a zoo, livestock, fur-bearing animals and domestic animals, including, but not limited to dogs, cats, mink, sheep, goats, swine, cattle, horses, mules and donkeys. The effect is obtained by administering an effective amount of one or a mixture of two or more of the carboxamides orally or parenterally to the animal. The carboxamides may be administered as such, or as an active ingredient of a conventional pharmaceutical formulation. They may be administered orally by any convenient means. Thus, they may be orally administered as a drench, by intubation, in the animal's food and water, in a food supplement or in a formulation expressly designed for administration of the drug. Suitable formulations include solutions, suspensions, dispersions, emulsions, tablets, boluses, powders, granules, capsules, syrups and elixirs. For parenteral administrations, they may be in the form of a solution, suspension, dispersion or emulsion. They can be administered in the form of an implant or other controlled sustained release formulation. Inert carriers, such as one or more of water, edible oil, gelatin, lactose, starch, magnesium stearate, talc or vegetable gum can be used. The dosage of the carboxamide needed to inhibit lipogenesis will depend upon the particular carboxamide used, and the particular animal being treated. However, in general, satisfactory results are obtained when the carboxamide can be administered in a dosage of from about 1 to about 500 milligrams per kilogram of the animal's body weight. The carboxamide can be administered in a single dose or in a series of doses in the same day, or over a period of days. For any particular animal, a specific dosage regimen should be adjusted according to the individual need, the particular carboxamide(s) used, and the professional judgment of the person administering or supervising the administration of the carboxamide. It is to be understood that the dosages set forth herein are exemplary only, and that they do not, to any extent, limit the scope or practice of the invention.

The effects of carboxamides of Formula I on the levels of cholesterol and triglycerides in the blood of a mammal were established as follows:

The procedure of Schurr et al., Lipids, 7, 68-74 (1972) was followed. In this procedure, hyperlipemia was induced in rats by intraperitoneal injection of Triton WR-1339 (oxyethylated tertiary-octylphenol/formaldehyde polymer, Ruger Chemical Co.), employing four groups of ten Sprague-Dawley strain male albino rats, each rat weighing 260-280 grams. After a 2-week stabilizing period, two groups (III and IV) were fasted for 24 hours. Then each rat was injected with a solution of the polymer in a saline vehicle (0.15 M sodium chloride solution; (62.5 milligrams of polymer per milliliter solution)), to give a dosage of 225 milligrams of polymer per kilogram of rat body weight. Two control groups (I and II) were also fasted and each rat received 2 milliliters of the saline vehicle. Groups II and IV received the test compounds in the vehicle, while Groups I and III received the vehicle only. The concentration of test compound in the vehicle was $8.22 \times 10^{-3}$ millimoles/milliliter. A total dose of 0.124 millimoles/kilogram of body weight was administered to the rats. Each rat received two 2-milliliter doses by gastric intubation, the first immediately after the polymer injection, and the other 20 hours later. Fasting was continued following injection of the polymer. 43 hours after the polymer was injected, the rats were anesthetized and blood was drawn from the abdominal aorta and centrifuged. Triglyceride content of the plasma was determined by the method of Eggstein, Klin. Wochenschr., 44, 267 (1966). Cholesterol content of the plasma was determined by the method of Holub et al., Clin. Chem., 18, 239 (1972). The results are shown in Tables 1 and 2.

Statistical analysis of the results show that:
(1) Comparison of Groups I and II indicate the effect of the drug on the normal rat. Compound 3 significantly lowered serum cholesterol levels in the normal rat (Table 1).
(2) Groups III and IV were both hyperlipemic, Group III being the control and group IV receiving the experimental drug. All three drugs lowered significantly the cholesterol level (III vs. IV). All three drugs also significantly lowered triglyceride levels in the hyperlipemic group (III vs. IV) (Table 2).

Table 1.

| | EFFECT OF TEST COMPOUNDS ON PLASMA CHOLESTEROL | | | |
|---|---|---|---|---|
| Compound | Control Group (I) | Drug-Treated Control (II) | Triton Hyperlipemic (III) | Drug-Treated Triton Hyperlipemic (IV) |
| 1 | 85.2 ± 11.97 | 87.3 ± 16.08 | 148.9 ± 40.25 | 126.6 ± 32.74 |
| 3 | 71.4 ± 8.04 | 62.8 ± 8.77 | 144.9 ± 72.88 | 102.6 ± 17.38 |
| 4 | 64.9 ± 12.04 | 63.4 ± 12.18 | 167.1 ± 72.76 | 109.6 ± 22.14 |

Table 2.

| | EFFECT OF TEST COMPOUNDS ON PLASMA TRIGLYCERIDES | | | |
|---|---|---|---|---|
| Compound | Control Group (I) | Drug-Treated Control (II) | Triton Hyperlipemic (III) | Drug-treated Triton Hyperlipemic (IV) |
| 1 | 25.7 ± 9.46 | 42.6 ± 7.26 | 115.2 ± 28.77 | 83.0 ± 33.54 |
| 3 | 43.8 ± 6.52 | 44.7 ± 10.87 | 142.5 ± 64.52 | 39.2 ± 4.80 |
| 4 | 33.1 ± 9.09 | 39.6 ± 8.24 | 136.8 ± 60.8 | 48.1 ± 16.8 |

I claim:
1. A method for reducing the levels of cholesterol and triglycerides in the blood of a mammal which comprises administering orally or parenterally to a mammal having an elevated blood cholesterol level, or an elevated blood triglyceride level, or both, an effective amount of a compound of the formula:

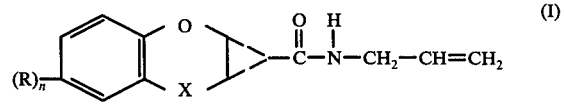

wherein $n$ is zero or one, R is lower halogen, and X is —O— or —$CH_2$—.

* * * * *

UNITED STATES PATENT AND TRADEMARK OFFICE
CERTIFICATE OF CORRECTION

PATENT NO. : 4,103,021
DATED : July 25, 1978
INVENTOR(S) : John B. Carr

It is certified that error appears in the above-identified patent and that said Letters Patent are hereby corrected as shown below:

Column 1 and column 6, in each, change the formula from

Signed and Sealed this

Sixteenth Day of January 1979

[SEAL]

Attest:

RUTH C. MASON
Attesting Officer

DONALD W. BANNER
Commissioner of Patents and Trademarks